(12) United States Patent
Ohkubo

(10) Patent No.: US 6,203,562 B1
(45) Date of Patent: Mar. 20, 2001

(54) APPLIANCE FOR MEDICAL TREATMENT

(76) Inventor: Seiko Ohkubo, 2-1-215, Kamisoshigaya, 4-chome, Setagaya-ku, Tokyo (JP)

( * ) Notice: Subject to any disclaimer, the term of this patent is extended or adjusted under 35 U.S.C. 154(b) by 0 days.

(21) Appl. No.: 09/203,332

(22) Filed: Dec. 2, 1998

(30) Foreign Application Priority Data

Dec. 4, 1997 (JP) .................................................. 9-348703

(51) Int. Cl.⁷ .................................................. A61B 17/00
(52) U.S. Cl. .............................. 606/204; 607/75; 607/99; 607/145
(58) Field of Search .................................... 607/2, 46, 50, 607/44, 75, 144, 145, 96, 98, 99; 600/372, 395; 601/15; 606/201, 204

(56) References Cited

U.S. PATENT DOCUMENTS

| | | | |
|---|---|---|---|
| 409,470 | * 8/1889 | Lawrance | ............................... 607/75 |
| 1,344,581 | * 6/1920 | Cooper | ................................. 607/144 |
| 4,173,229 | * 11/1979 | Halfon | ................................... 607/75 |
| 4,703,754 | * 11/1987 | Ibbott | ................................... 607/144 |
| 4,823,810 | * 4/1989 | Dervieux | ............................... 607/46 |
| 5,080,646 | * 1/1992 | Theeuwes et al. | ..................... 604/20 |
| 5,904,700 | * 5/1999 | Guo | ...................................... 606/204 |

* cited by examiner

Primary Examiner—Glenn K. Dawson
(74) Attorney, Agent, or Firm—Armstrong, Westerman, Hattori, McLeland & Naughton, LLP

(57) ABSTRACT

A medical treatment appliance to carry out therapeutical treatment by slightly pushing it to a skin of a patient, includes a grip portion, a conductor portion consisting essentially of electrically conductive metal(s), a "different metal" portion having an ionization tendency different from the electrically conductive metal(s), and optionally a crystal portion consisting essentially of a mineral, wherein the "different metal" portion, and optionally the crystal portion is(are) attached to the conductor portion.

11 Claims, 10 Drawing Sheets

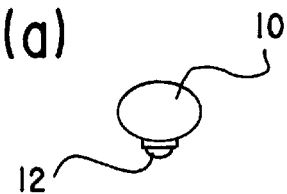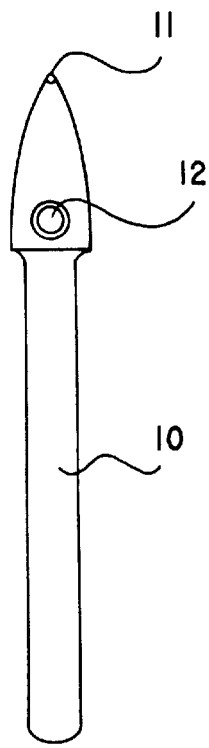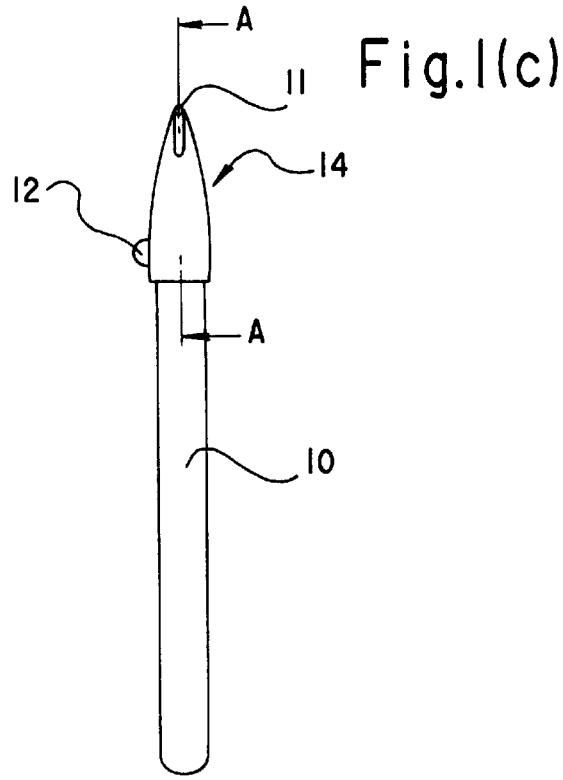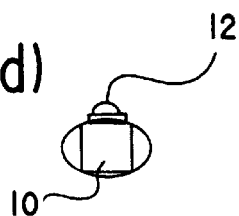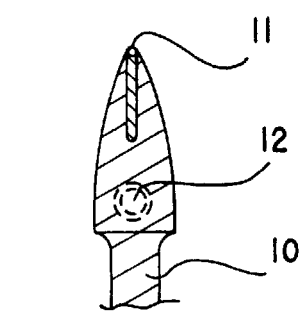

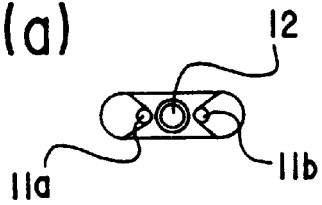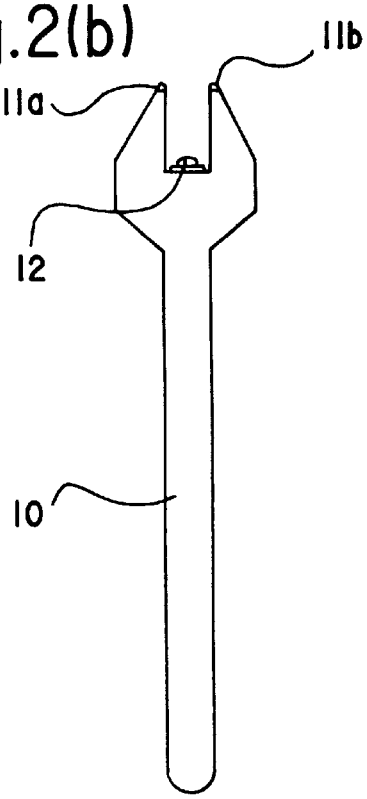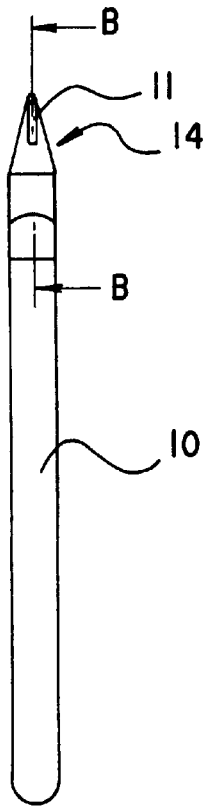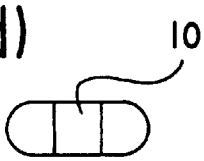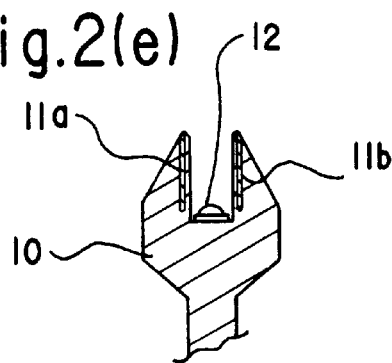

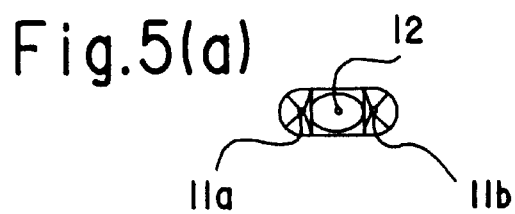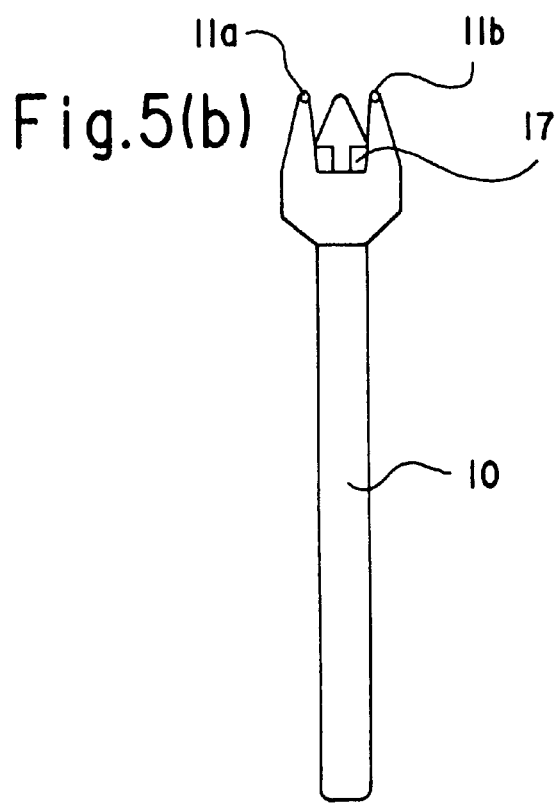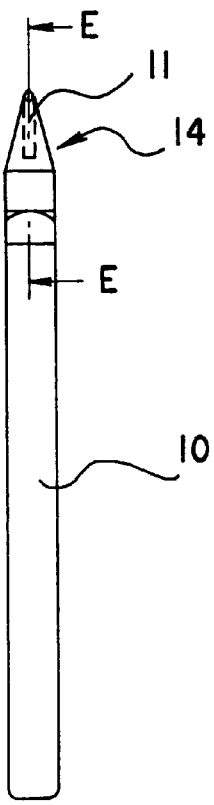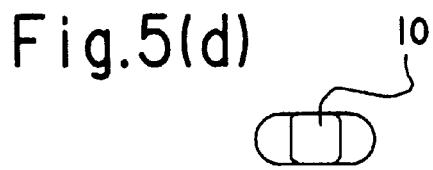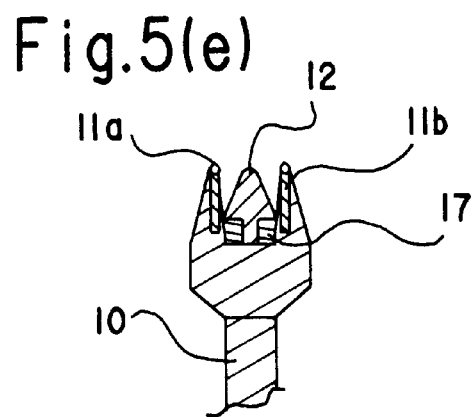

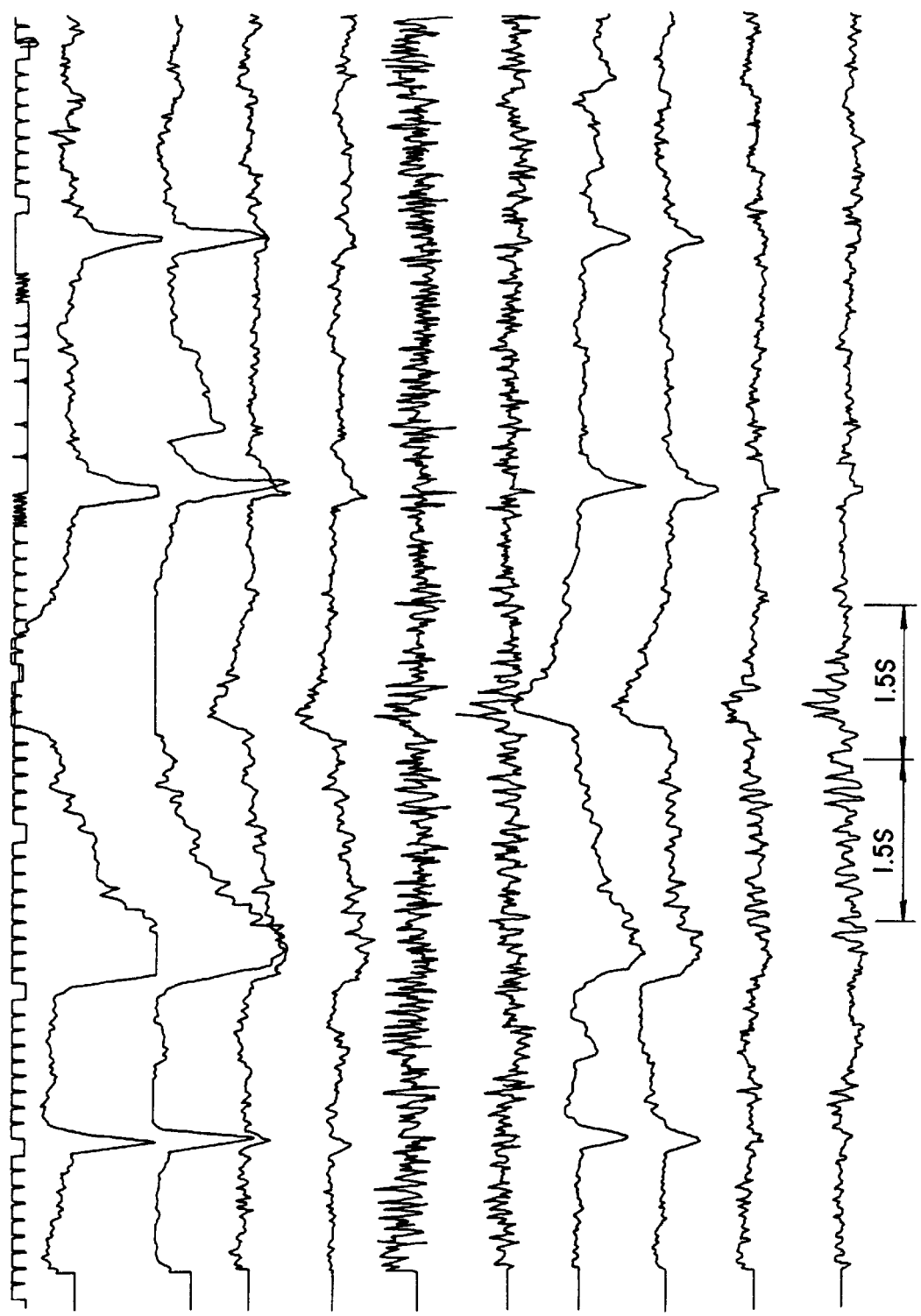

APPLIANCE FOR MEDICAL TREATMENT

BACKGROUND OF THE INVENTION

1) Field of the Invention

This invention relates to a special-structure appliance for medical treatment (hereinafter, medical treatment appliance) to push slightly to an affected portion or effective spot of a patient and thereby to strengthen natural healing power of human body and immediately to abate or relieve various pains such as muscular pain, neuralgia, headache, lumbago, stiff-neck pain, etc., and to remedy various ailments like asthma, etc. allergy troubles, post-surgical recovery of functions, and so on.

2) Prior Art

In conventional finger pressure therapy, a nerve is stimulated and a blood flow is accelerated by massaging an affected parts of a human body and an effective spot with human hand or fingers to mitigate the pain. The acupuncture therapy applies needle or moxa heating to an affected portion or an effective spot to perform treatment using heating power.

The conventional finger pressure therapy is effective in mitigating a stiff-shoulder pain, a muscular pain, etc., but it takes a long time. On the other hand, the acupuncture therapy has the problem of causing terror into a patient's heart, and resistance to it due to patient's excessive disliking for injection needles and apprehension of infection with AIDS virus (HIV-virus) due to direct insertion of needles into human body. In order to solve the above problems, this inventor has accomplished an invention of a finger pressure appliance in Japanese utility model application No. 9-10149.

This present invention solved above-mentioned problems and made further improvement over the invention of the Japanese utility model application No. 9-10149. The ailment can be cured without causing pain of human body, just by applying medical treatment appliance in contact with the affected portions and pushing slightly to a skin of a patient to enhance a natural healing power of human body and to relieve pains. Moreover, as it is absolutely safe in respect of infection with AIDS (HIV) virus, etc., due to contact, it gives patients a feeling of security. Besides, unlike electric medical instrument, it also does not use any external electricity. It is intended to introduce a medical treatment appliance that can give epoch-making treatment results.

SUMMARY OF THE INVENTION

As a result of ardent study of this inventor to solve the above-mentioned problems, this inventor has accomplished this invention of a medical treatment appliance to carryout therapeutical treatment by slightly pushing it to a skin of a patient, thereby solving those problems. The medical treatment appliance comprises a grip portion, a conductor portion consisting essentially of electrically conductive metal(s), a "different metal" portion with an ionization tendency different from that of the electrically conductive metal(s), and optionally a crystal portion essentially consisting of a mineral, wherein said "different metal" portion, and optionally said crystal portion is(are) attached to said conductor portion.

Here, the word "different metal" means a metal with a tendency of ionization different from that of the electrically conductive metal(s) in the conductor portion.

That is, this invention provide a medical treatment appliance to carry out therapeutical treatment by slightly pushing it to a skin of a patient, comprising a grip portion, a conductor portion consisting essentially of electrically conductive metal(s), a "different metal" portion having an ionization tendency different from said electrically conductive metal(s), and optionally a crystal portion consisting essentially of a mineral, wherein said "different metal" portion and optionally said crystal portion is(are) attached to said conductor portion.

In this invention, it is preferable that said grip portion has a thin, long, rod-like shape, and an acute angle-shaped conductor portion is provided at at least one end of said grip part, and said conductor portion is composed of at least one metal(s) selected from the group consisting of gold, silver, copper, aluminum, magnesium, platinum, iron, chromium, nickel, cobalt, tin, zinc, tungsten and titanium, and a "different metal" portion is attached to said conductor portion.

Further, it is preferable that said medical treatment appliance has a thin, long, rod-like shape, and said conductor portion is composed of at least one metal(s) selected from the group consisting of gold, silver, copper, aluminum, magnesium, platinum, iron, chromium, nickel, cobalt, tin, zinc, tungsten and titanium, and a "different metal" portion is attached to said conductor portion.

It is also preferable that said grip portion is a thin, long, rod-like shape, and an acute angle-shaped conductor is provided at at least one end of said grip portion, and a multiple of branched conductors starting from its other end is provided, and said conductor portion is made of at least one metal(s) selected from the group consisting of gold, silver, copper, aluminum, magnesium, platinum, iron, chromium, nickel, cobalt, tin, zinc, tungsten and titanium, and a "different metal" is attached to said conductor portion.

It is preferable that said "different metal" portion is composed of at least one metal(s) selected from the group consisting of gold, silver, copper, aluminum, magnesium, platinum, iron, chromium, nickel, cobalt, tin, zinc, tungsten, and titanium.

It is preferable that said crystal portion is pressure-fitted with said conductor portion, holding a tip height of said crystal portion at almost the same level as or a little lower level than a tip height of said "different metal" portion.

It is preferable that a hanger made of a rope or a chain or a mineral stone consisting essentially of birth stone is provided.

It is preferable that said grip portion is composed of synthetic resins.

It is preferable that said "different metal" portion is extruded from one side of said conductor portion composed of at least one metal(s) selected from the group consisting of gold, silver, copper, aluminum, magnesium, platinum, iron, chromium, nickel, cobalt, tin, zinc, tungsten and titanium, and said conductor portion is fixed to a base material, and an adhesive layer is applied onto a whole surface of said base material, excluding said "different metal" portion, and a layer of a releasing agent is laminated on a whole surface of said adhesive layer.

It is preferable that said "mineral" is a quartz, a tourmaline selected from the group consisting of schori, alkali tourmaline and dravite, hemimorphite, Rochelle salt or topaz.

BRIEF DESCRIPTION OF THE DRAWINGS

FIG. 1 shows Embodiment 1 of the medical treatment appliance where (a) is the plan view, (b) is the front view, (c) is the side view, (d) is the bottom view, and (e) is the sectional view of the appliance in drawing (c) at A—A line.

FIG. 2 shows Embodiment 2 of the medical treatment appliance where (a) is the plan view, (b) is the front view, (c) is the side view, (d) is the bottom view, and (e) is the sectional view of the appliance in drawing (c) at B—B line.

FIG. 5 shows Embodiment 5 of the medical treatment appliance where (a) is the plan view, (b) is the front view, (c) is the side view, (d) is the bottom view, and (e) is the sectional view of the appliance in drawing (c) at E—E line.

FIG. 9 shows an example of brain-wave measured during treatment of Clinical Example 2.

DETAILED DESCRIPTION OF THE INVENTION

Figure 3A:
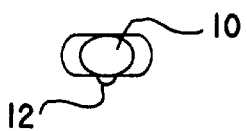
FIG. 3 shows Embodiment 3 of the medical treatment appliance where (a) is the plan view, (b) is the front view, (c) is the side view, (d) is the bottom view, and (e) is the sectional view of the appliance in drawing (c) at C—C line.
Figure 3B:
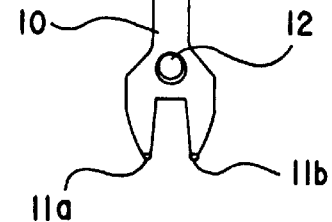
Figure 3C:
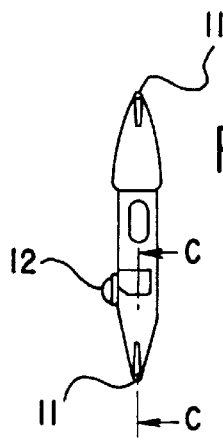
Figure 3D:
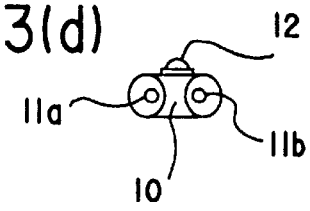
Figure 3E:
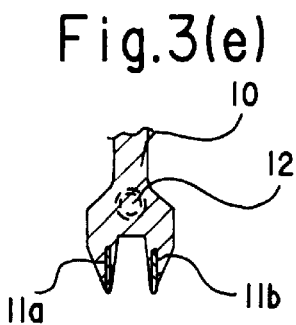
Figure 4A:
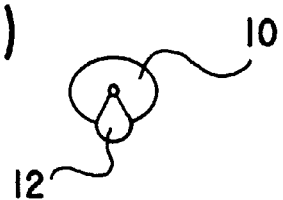
FIG. 4 shows Embodiment 4 of the medical treatment appliance where (a) is the plan view, (b) is the front view, (c) is the side view, (d) is the bottom view, and (e) is the sectional view of the appliance in drawing (c) at D—D line.
Figure 4B:
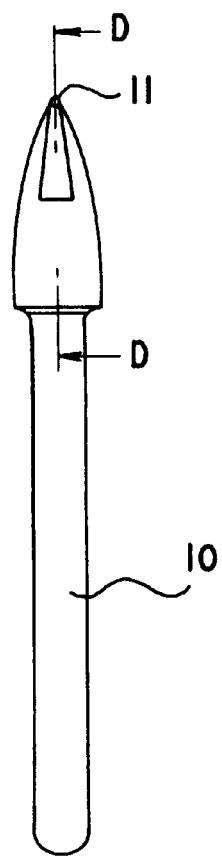
Figure 4C:
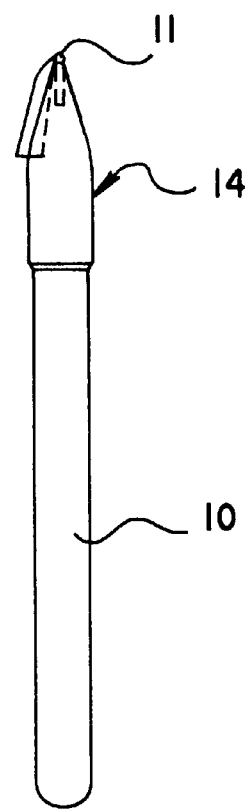
Figure 4D:
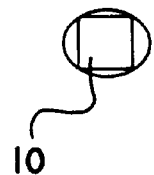
Figure 4E:
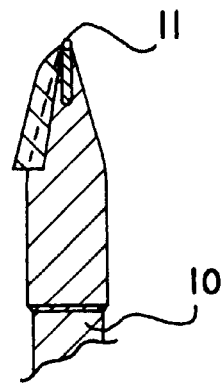
Figure 6A:
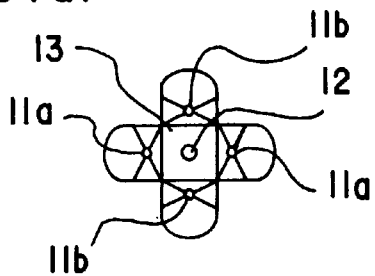
FIG. 6 shows Embodiment 6 of the medical treatment appliance where (a) is the plan view, (b) is the front view, (c) is the side view, (d) is the bottom view, and (e) is the sectional view of the appliance in drawing (c) at F—F line.
Figure 6B:
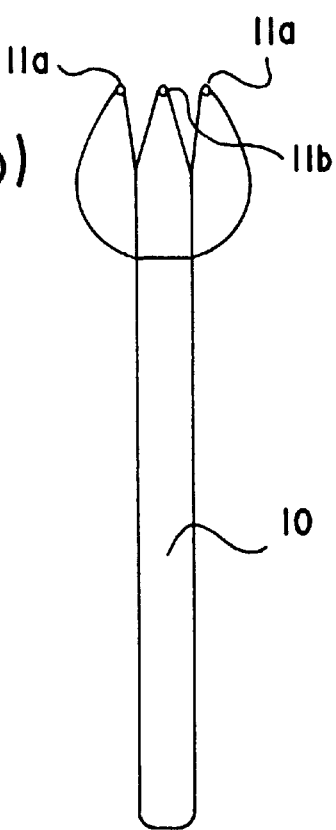
Figure 6C:
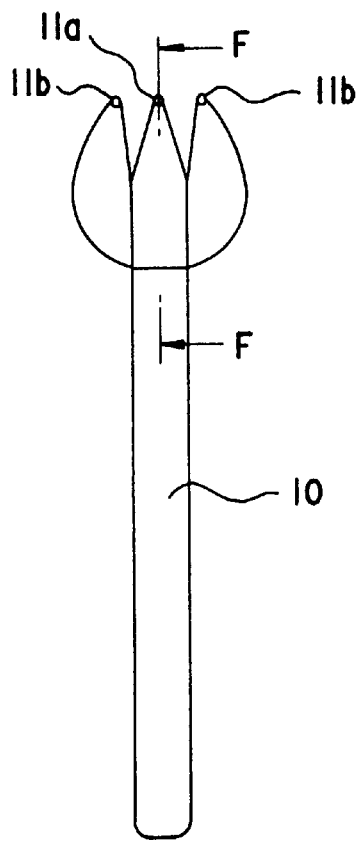
Figure 6D:
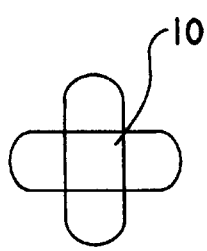
Figure 6E:
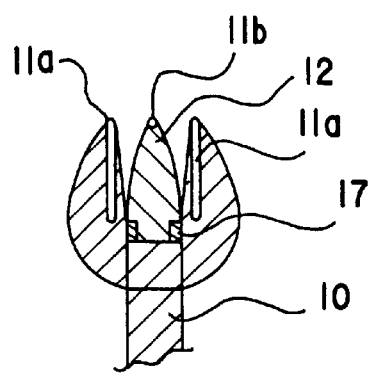
Figure 7A:
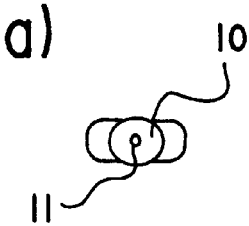
FIG. 7 shows Embodiment 7 of the medical treatment appliance where (a) is the plan view, (b) is the front view, (c) is the side view, (d) is the bottom view, and (e) is the sectional view of the appliance in drawing (c) at G—G line.
Figure 7B:
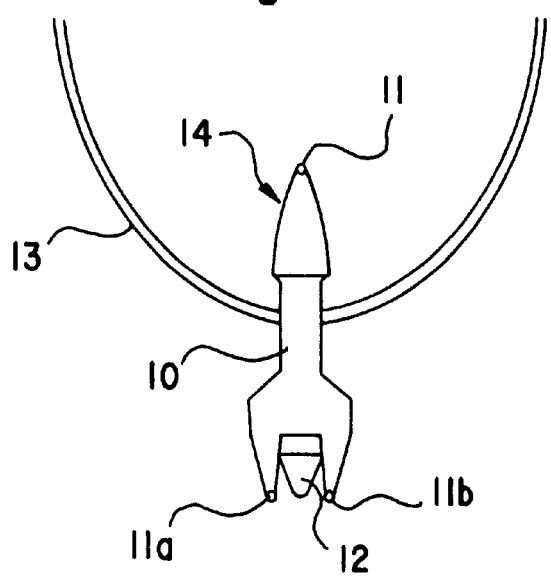
Figure 7C:
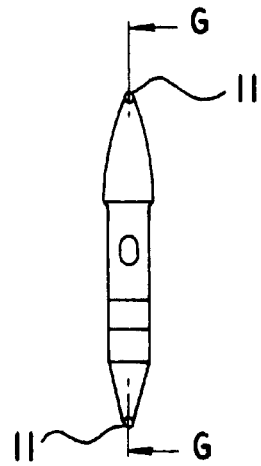
Figure 7D:
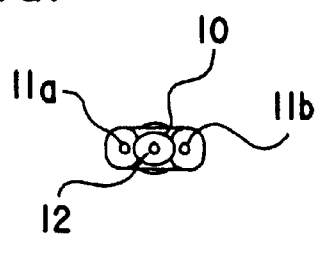
Figure 7E:
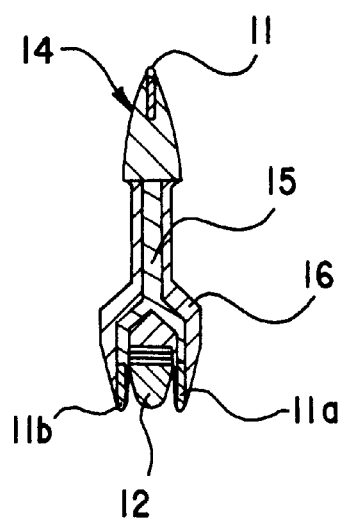

When the conductor portion and/or the "different metal" portion of the medical treatment appliance of this invention is brought in direct contact with a human skin or slightly pushed onto affected portions of a patient, a moisture in the neighborhood of skin of human body causes ionization of each metal forming the conductor portion and "different metal" portion, whereby an electric potential difference occurs between both metals according to an electric potential difference of standard electrode, resulting in a flow of a weak electric current to the affected portions of the patient through the conductor portion which has excellent electric conductivity.

When the grip portion of the medical treatment appliance is composed of electrically conductive metal(s), a weak electric current added an electric current of user's living body flows and acts on an electric current of patient's living body flowing through human body of the patient or a patient's nerve, which improves a blood flow and mitigates the pain and increases the natural healing power of human body.

Further, when the end of the medical treatment appliance including conductor portion and/or the "different metal" portion is slightly pushed onto affected portions of a patient, a nerve of the patient is stimulated and a blood flow is accelerated to mitigate the pain.

Thus, therapeutical treatment is carried out by both occurrence of a flow of a weak electric current and stimulation of nerve.

Moreover, there is provided a crystal portion of a mineral (for example: quartz, tourmaline, selected from the group consisting of schori, alkali tourmaline and dravite, hemimorphite, Rochelle salt, or topaz). The crystals activates cells of a human body by the action of said weak electric current and light, heat and friction to be provide from the exterior and increases the natural healing power of the human body, and as a result, the above-mentioned therapeutic effect above is assumed to be further enhanced.

Further, the crystal portion is pressure-attached to the grip portion by a burning method and fixed, and thereby, the crystal portion is compressed, and as a result, the crystal surface is electrified due to piezo-electric effect. When the conductor portion and/or the "different metal" portion is(are) slightly pushed to the affected portion, a tip of the crystal portion also simultaneously contacts a skin of a patient, and the electricity generated in the crystal portion is discharged into the body of the patient, and thus a weak electric current flows, which enhances said therapeutic effect.

It is very difficult to practically demonstrate the detailed mechanism concerning the action of the electric current of a living body. Therefore, the inventor measured the brain wave, pulse, heart-beat rate, oxygen saturation degree in blood ($SpO_2$) and body-temperature rise in patients during the use of the medical treatment appliance of this invention measured with a medical thermographic system.

The inventor is fully convinced that these data serve as powerful evidence to scientifically support the therapeutic effect of the medical treatment appliance of this invention. The details of these data will be described afterwards.

Next, typical embodiments of the medical treatment appliance of this invention are explained based on drawings.

The actual medical treatment appliance of Embodiment 1 shown in FIG. 1, is an example of one, wherein grip 10 is composed of synthetic resin, and has conductor portion 14 with an acute angle arrow shaped head at one end, and the tip part of conductor part 14 is provided with a "different metal" portion 11 inlaid therein, while crystal portion 12 consisting essentially of a mineral is provided in its neighborhood.

There is no particular restriction on the synthetic resins, etc. that form grip portion 10, provided that it is strong enough to withstand a pressure applied to the medical treatment appliance during its use. Examples thereof include thermo-plastic resins including high density polyethylene, polypropylene, polystyrene, polyacetal, vinyl chloride, As resin, ABS resin, acryl resin, polyamide, polyester, polycarbonate, fluorine resin, acetate resin, etc.; thermosetting resins including phenol resin, unsaturated polyester, melamine resin, and urea resins; various rubbers; and other composite materials of those materials and other additives and/or materials and conductors.

For improvement of design, organic and inorganic pigment may be added for coloring into the resins and the surface may be decorated with patterns. moreover, in order to transmit easily an electric current of a user's living body to a patient, electrically conductive metal powder, carbon fiber or carbon particles, etc. may be added. To protect the patient from various harmful bacteria, copper or silver type antibacterial agents may be added. In addition, to prevent degradation or resins, various antioxidants, light stabilizers, heat stabilizers, and anti-flame agents considered safety against fire, etc. may be added.

Conductor portion 14 is, for example, composed of at least one metal(s) selected from the group consisting of gold, silver, copper, aluminum, magnesium, platinum, iron, chromium, nickel, cobalt, tin, zinc, tungsten and titanium because, said metal(s) is(are) considered to have a high electrical conductivity and conduct weak electric current efficiently when in contact with a skin, and have rather low toxicity, and cause less corrosion or metallic allergy. Moreover, titanium can be used in this invention because of its excellent anti-metallic-allergy property, even though it is a little inferior to other metals in respect of electrical conductivity.

As the metals in "different metal" portion 11, except the harmful metals including lead, cadmium, etc., metals having different ionization tendency than those forming conductor portion 14 can be used to. Metals with larger difference in ionization tendency develop higher potential difference between them, for instance, if conductor portion 14 is composed of an alloy of gold with less ionization tendency, and "different metal" portion 11 is composed of aluminum with higher ionization tendency, a larger potential difference will be generated between both.

However, since electrical conductivity of aluminum, etc. deteriorates due to formation of oxidation film on the surface, it is desirable to wipe off the surface with polishing powder, etc., before use in order to improve the electrical conductivity. Moreover, the therapeutic effects can be enhanced by applying an electrolytic solution such as 0.9% - physiological saline solution, etc., in advance on the affected portion to be in contact with the medical treatment appliance.

The means of mounting the "different metal" portion 11 on conductor portion 14 is not necessarily restricted, but in view of increasing the flow of a weak electric current conducted mutually between an operator and the patient and increasing the electrical conductivity between both, a method of direct connection without interposing any non-conducting material such as adhesive material between both, e.g., a burning method is preferable. Further, in consideration of keeping the relative electric electrode potential between both and adjusting the flow of electricity through patient's skin in contact, a method of fixing with a non-conductor or an electrical semiconductor such as adhesive, etc., interposed between both is preferable.

The actual medical treatment appliance of Embodiment 2 in FIG. 2, is an example of one, wherein grip portion 10 is made of synthetic resin, etc., and its one end is conductor 14 made of an electrical conductive metal, the central tip of which is provided with the "different metal" portion 11 (11a and 11b) forked into 2 branches, and a crystal portion 12 composed of quartz, tourmaline, hemimorphite, Rochelle salt or topaz is provided at the middle portion of the starting point of the branches. The description of each structure is the same as in the case of the appliance of above-mentioned Embodiment 1.

The grip portion 10 of the appliance of Embodiment 3 in FIG. 3, is composed of synthetic resins, etc., and its both ends form conductor portion 14 made of electrical conductive metals. Its tip portion is provided with a "different metal" portion 11 (11a and 11b), one tip of which is acute angle-shaped, while the other is of bi-forked shape, and crystal portion 12 is provided near the surface of bi-forked conductor portion. Grip portion 10 is provided with hanger 13. The rest is the same as in the case of the practical medical treatment appliance of above-mentioned Embodiment 1.

In the appliance of Embodiment 4 in FIG. 4, conductor portion 14 is composed of a uniform electrically conductive metal, and an arrow-head like conductor portion 14 formed at one end is provided with crystal portion 12 tapered gradually towards the tip portion.

Conductor portion 14 of Embodiment 5 in FIG. 5, is composed of a uniform electrically conductive metal, and it has a conductor portion 14 forked out into two branches starting from at least one end of the grip portion 10, which have "different metal" portion 11a and 11b at their tips fixed with fixed portion 17. Except for the fact that crystal portion 12 is pressure-fitted at the center of the starting point of the two branches by a fixing device so that the tip is nearly at the same level a and/or a little lower level than the tip of conductor portion, the rest is the same as in the case of the practical medical treatment appliance of Embodiment 2.

In Embodiment 6 of the appliance in FIG. 6, conductor portion 14 is of a uniform electrically conductive metal, and it is branched into 4 conductors starting from at least one end of grip portion 10. Hanger 13 is used except for the fact that crystal portion 12 is pressure-fitted at the center of the starting point of the said branches so that the tip is nearly at the same height as and a little lower than that of the tip of conductor portion, the rest is the same as the case of Embodiment 5.

In Embodiment 7 of the medical treatment appliance shown in FIG. 7, arrow-shaped conductor portion 14 formed at one end of the appliance is connected to both "different metal" portions, 11a and 11b, formed at the other end by core material 15 made of an electrically conductive metal, and the surface of core material 15 is covered with synthetic resin portion 16, and thus grip portion 10 is formed. Crystal portion is pressure-fitted at the center of the starting point of the 2 branches with a fitting tool so that the tip is nearly at the same height as or a little lower level than that of the tip of conductor portion 14. Except for these, the rest is the same as explained in the case of Embodiment 3. The description on the synthetic resin is the same as in the case of Embodiment 1.

Figure 8A:
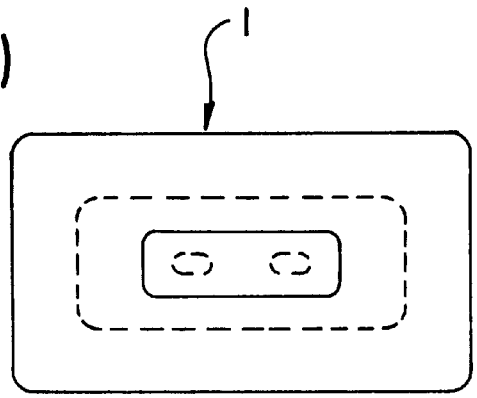
FIG. 8 shows Embodiment 8 of the medical treatment appliance where (a) is the plan view, (b) is the cross sectional view and (c) is the bottom view.
Figure 8B:
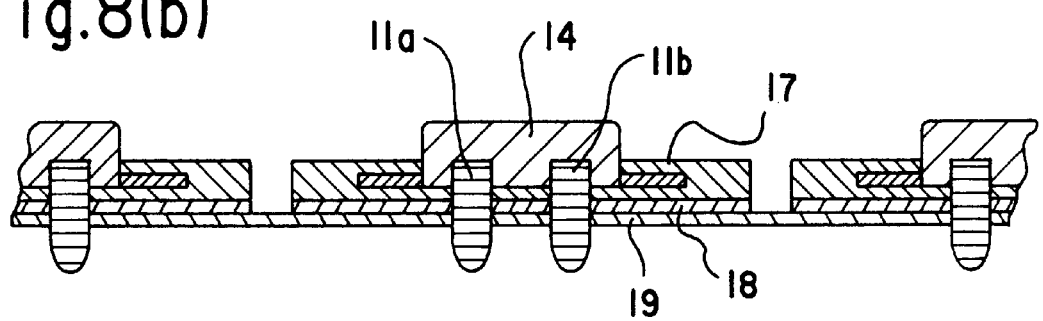
Figure 8C:
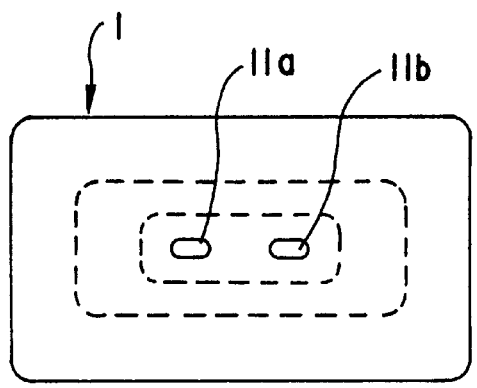

In Embodiment 8 shown in FIG. 8, as conductor portion 14 and/or the "different metal" portions 11a and 11b, fixed with fixed portion 17 is(are) formed on continuous releasing layer 19 adhered with adhesive layer 18 as described before, this medical treatment appliance can be used for treatment by properly taking it off from the releasing layer 19 at the time of use, and pressing and sticking the "different metal" portion to the affected portion of a patient. If necessary, the therapeutic effect can be enhanced by slightly pushing from the top of the main body.

PREFERRED EMBODIMENTS OF THE INVENTION

Examples of this invention are shown below, but it is not limited to Examples.

Example 1

In Embodiment 2 of the medical treatment appliance, the conductor portion 14 is made of so-called 18-carat gold alloy containing 75% by weight gold and 15% by weight silver, and 10% copper. Grip portion 10 is composed of a mixture of 1 part by weight of coloring pigment and 30 parts by weight of electrically conductive carbon fiber to 100 parts by weight of ABS resin. The "different metal" portions 11a and 11b were formed, inlaying by a burning method each metal piece of 100% by weight of copper and 100% by weight of aluminum on the tip of acute angle-shaped conductor 14. Thus, the medical treatment appliance A was obtained.

Example 2

In Embodiment 4, conductor portion 14 is composed of a uniformly pure gold, and a part of an aluminum piece is fixed in inlaid condition at the tip of arrow-like shape conductor portion 14 of one end of the main body. The tourmaline crystal portion 12 is pressure-fitted by a burning method in the vicinity of the "different metal" portion 11 of aluminum. Thus, the medical treatment appliance A was formed. Then, except for the pressure-fixing of a copper piece instead of aluminum on the "different metal" portion 11, the medical treatment appliance B also was obtained in the same manner as in the medical treatment appliance A.

Example 3

In Embodiment 5 of the medical treatment appliance, conductor portion 14 is composed of a uniformly pure gold, and a metal piece containing 100% by weight of platinum was inlaid at one terminal of the 2 branches of one end of grip portion 10, and then, a side of a metal piece of 100% by weight aluminum was inlaid by a burning method, forming each "different metal" portions 11a and 11b provided there. And then, crystal portion 12 of quartz, tourmaline, hemimorphite, Rochelle salt or topaz was fixed by pressure in the vicinity of the starting point of the branches. Thus, the medical treatment appliance C was obtained.

Example 4

In Embodiment 6 of the medical treatment appliance, conductor portion 14 is composed of a uniformly pure gold, and a side of a metal piece of 100% by weight platinum and a side of a metal piece of 100% by weight aluminum were mutually inlaid by a burning method into the 4 branches starting from grip portion 10 to form each "different metal" portions 11a and 11b, and the crystal portion 12 of quartz was set by a burning method near the starting point of the branches. Thus the medical treatment appliance D was obtained.

APPLICATION EXAMPLE

After "different metal" portion 11 of the medical treatment appliance of the Examples 1–4 is brought in contact with the affected portions and effective portions, slight push is applied for 2–3 seconds, and then, the medical treatment appliance 1 is detached from the body of the patient, and immediately thereafter, the same operation as before is repeated for 10–15 minutes.

At the time of applying slight push with the "different metal" portion by bringing it in contact, in case of an medical treatment appliance mounted with crystal portion 12 at the desired position, when the tip of the crystal portion is slightly in contact with the skin of the patient, the effect is enhanced, and thus, preferable effect is provided. Besides, the therapeutic effect can be enhanced by accelerating the metal ionization with proper application of an electrolytic solution such as 0.9%-physiological saline solution, etc., on the skin of the patient in contact with the medical treatment appliance.

CLINICAL EXAMPLES

The inventor has so far carried out trial treatment of several tens of specific patients with their consent, using the medical treatment appliance of this invention, and obtained the results of curing the ailments. The typical cases, selected from the actual cases of treatment, are described hereunder.

Clinical Example 1 (Treatment of a Case of Muscular Membrane Laceration)

A 31 year old male swimmer had a wide back muscle injury during swimming, and it was hampering his daily life. The whole back of the patient was given a trial treatment with the medical treatment appliances C and D of the Examples 3 and 4 embodying this invention, holding them with both hands, and applying slight push. The pain was relieved by about 80% at the initial trial, and surprisingly, the symptom completely disappeared after the second treatment.

Clinical Example 2 (A Case of Treatment of Strong Sensitivity to Cold)

A 28-year old female had been suffering from over sensitivity to cold and had been treated with drugs every other week, but there was no recovery. Both of her legs were treated with the medical treatment appliance D of Example 4 by pressing it on the legs, and after about 5–10 minutes, the temperature of both the legs rose by about 6.4° C. as confirmed by a thermograph. After that, the treatment was continued on the whole body once a week. Then the blood circulation activities improved, and the symptom was remarkably abated.

Clinical Example 3 (A Case of Treatment of Inter-Vertebral Disc Hernia)

A 50-year old female had been suffering from pain and numbness at the left lower limb starting from the waist part since half an year ago. The case was diagnosed as the hernia of L4–5, and she was taking anti-inflammatory analgesic drug. When the case was treated by using the medical treatment appliance C of Example 3, holding one each by the left and the right hand, and applying pressure on the affected parts, the pain was mitigated by half after the first treatment, and it was relieved fully after the treatment for 7 times. Even after 3 months now, no relapse of it has been observed.

Clinical Example 4 (A Case of Treatment of Carpal Joint Syndrome)

A 34-year old female had developed pain and numbness in the palm and the finger-tips after playing tennis. Because of severe pain, it was difficult for her to bend or stretch the fingers. However, the above mentioned treatment was given by holding the medical treatment appliances A and B of Examples 1 and 2 by the left and the right hand respectively, and alternately contacting the inside of the right forearm part, carpal joint and the palm. Then, the pain was relieved by about 60%. After application of the therapy 3 times, she could bend and stretch the fingers painlessly.

Clinical Example 5 (A Case of Treatment of Back (Dorsal) Pain and Lumbago)

This is a male baseball player (out-fielder) suffering from the dorsal (back) pain and lumbago. When the treatment was given, using the medical treatment appliance A of Example 1, after one day, the affected parts warmed up, and pain was mitigated. Moreover, when the same treatment was given everyday, the pain disappeared completely on the 3rd day, and surprisingly, he recovered on the 4th day to the extent that he could throw the ball and swing the bat.

Clinical Example 6 (A Case of Treatment of a Long-Term Headache)

This is a female patient who had been suffering from headache for several years, and was taking drugs. When the patient was treated with the appliances A and B of Examples 1 and 2, holding them by left and the right hand respectively, and contacting the neck and the head parts, lightly applying pressure and repeating the same therapy as above, the pain was mitigated on the first day, and the headache disappeared on the third day. The headache did not relapse even after the drug was stopped.

Clinical Example 7 (A Case of Treatment of Asthma)

This is a male patient suffering from asthma. The same treatment as mentioned before was applied, holding the medical treatment appliances C and D of Examples 3 and 4 by the left and the right hand respectively and applying light pressure with them at the patient's left and right chest parts. The initial asthmatic attack was mitigated, and it stopped on the 3rd day. After that, the treatment was carried out once a week for a month, but the ailment did not relapse.

Example of Practical Performance

With the cooperation of specialists, the inventor measured the patient's brain wave, pulse rate, heart-beat rate, and oxygen saturation degree in blood ($SPO_2$) and body-temperature-rise during the use of the medical treatment appliance of this invention by thermography. Immediately after the use of the medical treatment appliance of this invention, alpha-wave and Beta-wave appeared. The pulse rate and heart-beat rate increased, and also the temperature of the affected part rose within 5 to 10 minutes after the use, even though there was no such occurrence when pressure was applied to the affected part by a simple wooden rod (not shown in drawing). The brain-wave and the heart-beat rate are shown in FIGS. 9 and 10 respectively.

These data are explained below.

FIG. 9 shows an ex ample of brain-wave measured during the treatment in the case of clinical Example 6 "A case of treatment of long-term headache" mentioned earlier. The generation of alpha-wave (brain wave of frequency range of 8–13 Hz) and Beta-wave (brain-wave of frequency range of 13–40 Hz) about 3 seconds after starting the measurement could be confirmed from FIG. 9. From this result, it can be inferred, from the point of view of cerebral (brain) physiology, that there is a change in the action of the cerebral cortex due to the electric stimulus to the human nerve by the medical treatment appliance of this invention. As a result, it is estimated that the therapeutic effect is enhanced because of strengthening of the natural healing power by normalizing the electric activity of synapses and the secretion of the nerve-conductive materials.

Figure 10:
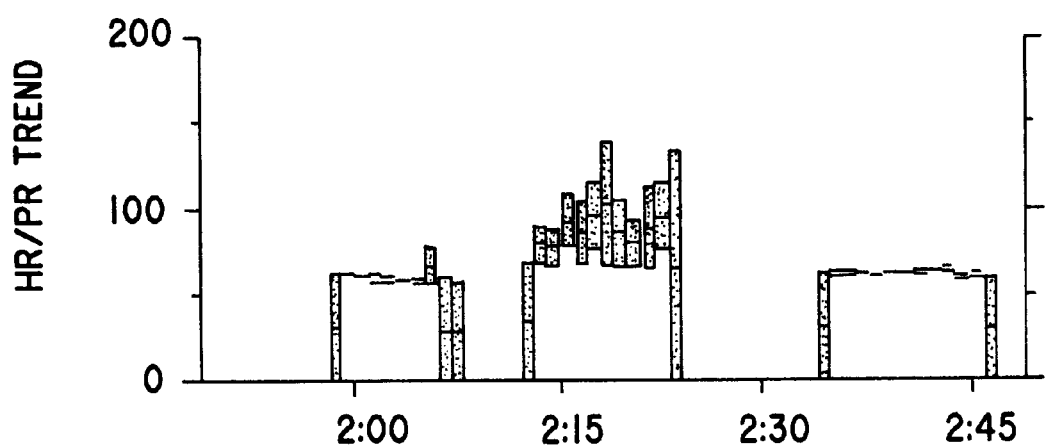
FIG. 10 is a graph showing the heart beat rate.

FIG. 10 and Tables 3 and 4 show the heart-beats rate, pulse rate of N1BP list record and oxygen saturation degree in blood ($SpO_2$, %) during the treatment of the typical clinical Example 2 "A case of treatment of strong sensitivity to cold". Tables 1 and 2 show the same result of measurement of the above items during the treatment of the typical clinical Example 3 "A case of treatment of intervertebral disc hernia". This is an experiment where the measurement was done with BSM-7105 made by Nippon Koden Industry Ltd.

It is confirmed from FIG. 10 that the heart-beat rate increased by 50–100% in about 2 to 15 seconds after the start of the treatment. Tables 3 and 4 confirmed that the pulse (beat/min) increased by 30–70% in about 2 to 6 seconds after the start of the therapy.

Similarly, tables 1 & 2 show that the pulse rate increased by about 60% in about 5 to 10 minutes after the starting of the therapy. Data of the above-mentioned Tables 1–4 and FIG. 10 were obtained the same time as the data of the thermograph, and the measurement was done at the same measuring port of the data displayed on the thermograph. The thermogram (body temperature graph) measurement on a total of 6 cases at each part of ankle, hand, back and hip showed a rise of temperature by 3.3 to 6.4° C. in 5 to 10 minutes after the start of the therapy. Some of these results reveal that there is improvement in the blood flow trouble after the use of this medical treatment appliance in the cases that had trouble in blood flow or had a poor flow before use of the medical treatment appliance. As mentioned later, it is also said that pain is relieved with the improvement of the blood flow as above.

Next, as a comparative example, when pressure was applied with a simple wooden rod, there was no rise in temperature, and on the contrary, the temperature fell in about 5 to 10 minutes after the start of using it.

The mechanism of relieving pain is complicated, but it is closely related to the improvement in blood circulation in many cases. It is also reported that blood circulation is a great motive force to accelerate the healing of injury ("Wonder of laser medicine" by Kodansha Pub. Inc.P.176). Moreover, in oriental medicine, temperature rise is measured at the affected human parts by similar methods for judging the effects of therapy. It was absolutely a rare phenomenon to observe a temperature rise by about 3.3 to 6.4° C. as mentioned above within a short time of about 5 to 10 minutes after starting the use of this medical treatment appliance.

In order to prove the efficacy of this medical treatment appliance from other perspective, the inventor conceived a means of confirming the existence of a weak electric current between the said conductor and "different metal" part with different ionization tendency, and tried its observation. As a result, when a weak electric current flowed with a physiological saline solution being dropped, the discoloration test paper confirmed the actual discoloration.

The medical treatment appliance of this invention, which is of the structures mentioned earlier is effective in treating various ailments such as asthma, etc. allergy troubles, post-surgical recovery, etc. by contacting the affected parts of the patients and lightly applying slight push to enhance the natural healing power and to immediately abate or relieve different pains such as muscular pain, neuralgia, headache, lumbago, stiff-neck pain, etc.

Particularly, when the medical treatment appliance of a structure, wherein the crystal portion is of quartz, tourmaline, calamine, Rochelle salt, or topaz contacts the affected parts of patients, changes occur in the body of the patients instantly, resulting in immediate therapeutic effect. As there is neither needle, nor surgical knife to be applied to the body, it is also safe against AIDS infection, and gives the patients a sense of security which has the effect of actively promoting the healing. In addition, the design and economy have been improved by using synthetic resin in the grip portion, and as the appliances with a hanger can easily be carried all the time, they are convenient. Those appliances provided with adhesive layer on the back-side are effective for continued therapeutic effect. Moreover, as outside electricity is not used unlike in the case of electric therapeutic instrument, it can be readily used outdoor without electricity provision even in emergency or in the countries where the voltage is different from each country, and there is also no need of any maintenance.

TABLE 1

| | BED-001 | | '97/11/20 | 3:24 | |
|---|---|---|---|---|---|
| DATE | 11/20 | | 11/20 | 11/20 | 11/20 |
| TIME | 2:57 | | 2:58 | 2:58 | 3:00 |
| PULSE | 66 | | 66 | 66 | 64 |
| SPO$_2$ | 98 | | 98 | 98 | 98 |

TABLE 2

| | | | BED-001 '97/11/20 3:24 | | | | |
|---|---|---|---|---|---|---|---|
| DATE | 11/20 | 11/20 | 11/20 | 11/20 | 11/20 | 11/20 | 11/20 | 11/20 |
| TIME | 3:01 | 3:02 | 3:03 | 3:04 | 3:05 | 3:06 | 3:07 | 3:08 |
| PULSE | 65 | 65 | 65 | 64 | 103 | 107 | 64 | 74 |
| SPO$_2$ | 97 | 98 | 98 | 97 | 97 | 98 | 98 | 98 |

TABLE 3

| | BED-001 | '97/11/20 | 2:31 |
|---|---|---|---|
| DATE | 11/20 | 11/20 | 11/20 |
| TIME | 2:14 | 2:15 | 2:16 |
| PULSE | 69 | 68 | 91 |
| SPO$_2$ | 99 | 99 | 99 |

TABLE 4

| | | | BED-001 '97/11/20 2:31 | | | | |
|---|---|---|---|---|---|---|---|
| DATE | 11/20 | 11/20 | 11/20 | 11/20 | 11/20 | 11/20 | 11/20 | 11/20 |
| TIME | 2:17 | 2:18 | 2:19 | 2:20 | 2:21 | 2:22 | 2:23 | 2:24 |
| PULSE | 77 | 103 | 118 | 89 | 75 | 88 | 88 | 87 |
| SPO$_2$ | 99 | 98 | 96 | 97 | 98 | 97 | 97 | 98 |

What is claimed is:

1. A medical treatment apparatus for therapeutical treatment by contact with a patient's skin, consisting essentially of:
   a grip portion having a rod-like shape having two ends;
   a conductor portion having forked shape and attached to at least one end of the grip portion, the conductor portion consisting essentially of at least one electrically conductive metal; and
   a different metal portion attached to the conductor portion, the different metal portion having an ionization tendency different from that of said at least one electrically conductive metal thereby causing an electric potential difference between the conductor portion and the different metal portion when the medical treatment apparatus is in contact with the patient's skin,
   wherein the grip portion is ABS resin; the conductor portion is an alloy containing 75% by weight gold, 15% by weight silver, and 10% by weight copper; and a first different metal portion is 100% by weight copper located on a tip of a first end of the forked portion and a second different metal portion is 100% by weight aluminum located on a tip of a second end of the forked portion.

2. The medical treatment apparatus of claim 1, wherein the apparatus causes stimulation of the patient's skin when the medical treatment apparatus is pushed slightly against the patient's skin.

3. A medical treatment apparatus for therapeutical treatment by contact with a patient's skin, consisting essentially of:
   a grip portion having two ends, the grip portion composed of a synthetic resin selected from the group consisting of high density polyethylene, polypropylene, polystyrene, polyacetal, vinyl chloride, ABS resin, acryl resin, polyamide, polyester, polycarbonate, fluorine resin, acetate resin, phenol resin, unsaturated polyester, melamide resin, and urea resins;
   a conductor portion attached to at least one end of the grip portion, the conductor portion is composed of at least one metal selected from the group consisting of gold, silver, copper, aluminum, magnesium, platinum, iron, chromium, nickel, cobalt, tin, zinc, tungsten, and titanium; and
   a different metal portion inlaid in and attached directly to the conductor portion, the different metal portion composed of at least one metal selected from the group consisting of gold, silver, copper, aluminum, magnesium, platinum, iron, chromium, nickel, cobalt, tin, zinc, tungsten, and titanium and the different metal portion having an ionization tendency different from that of said at least one electrically conductive metal thereby causing an electric potential difference between the conductor portion and the different metal portion when the medical treatment apparatus is in contact with the patient's skin.

4. A medical treatment apparatus for therapeutical treatment by contact with a patient's skin, consisting essentially of:
   a grip portion having two ends;
   a conductor portion attached to at least one end of the grip portion, the conductor portion consisting essentially of at least one electrically conductive metal;
   a crystal portion having piezoelectric properties composed of a mineral selected from the group consisting of quartz, schori, alkali tourmaline, dravite, hemimorphite, Rochelle salt and topaz attached to the conductor portion; and
   a different metal portion attached to the conductor portion, the different metal portion having an ionization tendency different from that of said at least one electrically conductive metal thereby causing an electric potential difference between the conductor portion and the different metal portion when the medical treatment apparatus is in contact with the patient's skin.

5. The medical treatment apparatus of claim 4, wherein the conductor portion is composed of at least one metal selected from the group consisting of gold, silver, copper, aluminum, magnesium, platinum, iron, chromium, nickel, cobalt, tin, zinc, tungsten and titanium.

6. The medical treatment apparatus of claim 4, wherein the different metal portion is composed of at least one metal selected from the group consisting of gold, silver, copper, aluminum, magnesium, platinum, iron, chromium, nickel, cobalt, tin, zinc, tungsten, and titanium.

7. The medical treatment apparatus of claim 4, wherein the grip portion is composed of synthetic resins selected from the group consisting of high density polyethylene; polypropylene; polystyrene; polyacetal; vinyl chloride; ABS resin; acryl resin; polyamide; polyester; polycarbonate; fluorine resin; acetate resin; phenol resin; unsaturated polyester; melamide resin; urea resins.

8. The medical treatment apparatus of claim 4 wherein the grip portion is composed of an electrically conductive metal.

9. The medical treatment apparatus of claim 4, further comprising a means for hanging the medical treatment apparatus, the means for hanging being attached to the grip portion.

10. A medical treatment apparatus for therapeutical treatment by contact with a patient's skin, consisting essentially of:

a grip portion having two ends;

a conductor portion attached to at least one end of the grip portion, the conductor portion consisting essentially of at least one electrically conductive metal; and a different metal portion inlaid in and attached directly to the conductor portion, the different metal portion having an ionization tendency different from that of said at least one electrically conductive metal thereby causing an electric potential difference between the conductor portion and the different metal portion when the medical treatment apparatus is in contact with the patient's skin and causing stimulation of the patient's skin when the medical treatment apparatus is pushed slightly against the patient's skin.

11. A medical treatment apparatus for therapeutical treatment by contact with a patient's skin, consisting essentially of:

a grip portion having two ends;

a conductor portion attached to at least one end of the grip portion, the conductor portion consisting essentially of at least one electrically conductive metal; and a different metal portion inlaid in and attached directly to the conductor portion, the different metal portion having an ionization tendency different from that of said at least one electrically conductive metal thereby causing an electric potential difference between the conductor portion and the different metal portion when the medical treatment apparatus is in contact with the patient's skin.

* * * * *

UNITED STATES PATENT AND TRADEMARK OFFICE
CERTIFICATE OF CORRECTION

PATENT NO.     : 6,203,562 B1                                            Page 1 of 1
DATED          : March 20, 2001
INVENTOR(S)    : Ohkubo, Seiko It is certified that error appears in the above-identified patent and that said Letters Patent is hereby corrected as shown below:

<u>Title page,</u>
Item [76], Inventor, please change the name of the inventor from Seiko OHKUBO" to
-- Nene MURAKOSHI -- and change the address of the inventor from "2-1-215, Kamisoshigaya, 4-chome, Setagaya-ku, Tokyo, Japan" to -- 260-9, Kosugi-cho 3-chome Nakahara-ku, Kawasaki-city, Kanagawa, 211-0064, Japan --.

Signed and Sealed this

Twentieth Day of April, 2004

JON W. DUDAS
*Acting Director of the United States Patent and Trademark Office*